US006936597B2

(12) United States Patent
Greenwald et al.

(10) Patent No.: US 6,936,597 B2
(45) Date of Patent: Aug. 30, 2005

(54) PRODRUGS OF ANTICANCER AGENTS EMPLOYING SUBSTITUTED AROMATIC ACIDS

(75) Inventors: Richard B. Greenwald, Somerset, NJ (US); Yun H. Choe, Green Brook, NJ (US)

(73) Assignee: Enzon, Inc., Piscataway, NJ (US)

( * ) Notice: Subject to any disclaimer, the term of this patent is extended or adjusted under 35 U.S.C. 154(b) by 291 days.

(21) Appl. No.: 10/103,323

(22) Filed: Mar. 21, 2002

(65) Prior Publication Data

US 2002/0193409 A1 Dec. 19, 2002

Related U.S. Application Data

(60) Provisional application No. 60/278,298, filed on Mar. 23, 2001.

(51) Int. Cl.$^7$ .................... A61K 31/70; A61K 31/7068; C07H 19/06; C07C 63/00

(52) U.S. Cl. ......................... 514/49; 514/332; 514/567; 514/616; 514/637; 514/568; 536/28.5; 548/100; 548/556; 544/239; 544/298; 544/1; 546/338; 546/313; 546/290; 546/300; 546/301; 546/262; 562/405; 562/426; 562/465; 562/443; 562/450; 562/457; 562/458; 564/156

(58) Field of Search .............................. 514/49, 43, 42, 514/332, 567, 568, 637, 616; 562/457, 426, 465, 405, 443, 450, 458; 564/156; 536/28.5; 548/100, 556; 544/239, 298; 546/338, 313, 290, 300, 301, 262

(56) References Cited

U.S. PATENT DOCUMENTS

| | | |
|---|---|---|
| 5,965,119 A | 10/1999 | Greenwald et al. |
| 6,180,095 B1 | 1/2001 | Greenwald et al. |
| 6,303,569 B1 | 10/2001 | Greenwald et al. |

FOREIGN PATENT DOCUMENTS

| | | |
|---|---|---|
| WO | WO 99/30561 | 6/1999 |
| WO | WO 01/17501 A1 * | 3/2001 |

OTHER PUBLICATIONS

Butterworth et al. (Journal of Medicinal Chemistry (1987), 30 (8), 1295–1302) (abstract sent).*

Schulz et al. (Journal of Macromolecular Science, Pure and Applied Chemistry (1993), A30 (1), 91–103) (abstract sent).*

Burger et al. (Journal of Organic Chemistry (1995), 60 (23), 7382–3) (abstract sent).*

Underliner et al., WO 2001017501 A1 (Mar. 15, 2001) (Abstract sent).*

* cited by examiner

*Primary Examiner*—James O. Wilson
*Assistant Examiner*—Michael C. Henry
(74) *Attorney, Agent, or Firm*—Muserlian Lucas & Mercanti

(57) ABSTRACT

Polymeric prodrugs of the formula:

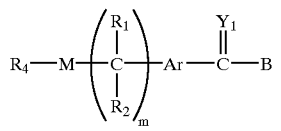

wherein

B is selected from the group consisting of OH, leaving groups, residues of amine-containing moieties and a residues of hydroxyl-containing moieties;

$Y_1$ is selected from the group consisting of O, S, and $NR_5$;

M is $NR_3$, O or S;

Ar is a moiety which when included in Formula I forms a multi-substituted aromatic or heteroaromatic hydrocarbon or a multi-substituted heterocyclic group;

(m) is zero or a positive integer;

$R_{1-3}$ and $R_5$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and $R_4$ is a polymeric residue;

as well as methods of making and using the same are disclosed.

24 Claims, 2 Drawing Sheets

(i) T-PEG (2), pyridine. (ii) 2-Mercaptothiazoline (4), EDC, DMAP, DCM. (iii) Drug, pyridine.

(3)

7: Drug = O-Paclitaxel
a: m = 1
b: m = 0

PRODRUGS OF ANTICANCER AGENTS EMPLOYING SUBSTITUTED AROMATIC ACIDS

CROSS-REFERENCE TO RELATED APPLICATIONS

This application claims the benefit of priority from U.S. Provisional Patent Application Ser. No. 60/278,298, filed Mar. 23, 2001, the contents of which are incorporated herein by reference.

TECHNICAL FIELD

The present invention relates to prodrugs. In particular, the invention relates to polymeric-based prodrugs having reversible linkages involving aromatic moieties and biologically-active materials such as enzymes, proteins, and other useful drugs or pharmaceuticals.

BACKGROUND OF THE INVENTION

Over the years, several methods of administering biologically-active materials to mammals have been proposed. Many biologically-active materials, e.g., chemical compounds that can be described as medicinal agents, drugs, pharmaceuticals, etc., are available as water-soluble salts and can be included in pharmaceutical formulations relatively easily. Problems arise when the desired biologically-active material is either insoluble in aqueous fluids or is rapidly degraded in vivo. For example, alkaloids are often especially difficult to solubilize.

One way to solubilize biologically-active materials is to include them as part of a soluble prodrug. Prodrugs include chemical derivatives of a biologically-active chemical compound which, upon administration, eventually liberate the biologically-active material (hereinafter referred to e.g., as the drug or parent compound), in vivo. Linking the parent compound with a modifier moiety or moieties, to form a prodrug, allows the artisan to modify the onset and/or duration of action of the parent compound, in vivo. The artisan can also formulate prodrugs that can modify the transportation, distribution or solubility of a drug in the body. Furthermore, prodrug formulations often reduce the toxicity and/or otherwise overcome difficulties encountered when administering pharmaceutical preparations. Typical examples of prodrugs include those based upon organic phosphates, esters of alcohols, thioalcohols and other art-known derivatives. See *Remington's Pharmaceutical Sciences*, 16th Ed., A. Osol, Ed. (1980) (the disclosure of which is incorporated by reference).

Prodrugs are often biologically inert or substantially inactive forms of the parent compound. The rate of release of the active drug, i. e., the rate of hydrolysis of the prodrug, is influenced by several factors, but especially by the type of bond joining the parent drug to the modifier. Care must be taken to avoid preparing prodrugs which are eliminated through the kidney or reticular endothelial system, etc. before a sufficient amount of hydrolysis of the parent compound occurs. By incorporating a polymer as part of the prodrug system, one can increase the circulating half-life of the drug.

Thus, there continues to be a need for additional novel polymeric prodrug technologies. The present invention addresses this need.

SUMMARY OF THE INVENTION

In some aspects of the invention, polymeric-linked prodrugs of Formula (I) and (II) are provided:

(I)

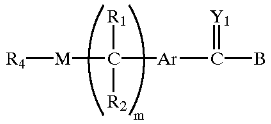

(II)

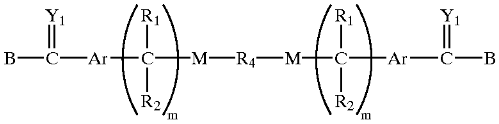

wherein

B is a OH, a leaving group, a residue of an amine-containing moiety or a residue of a hydroxyl-containing moiety;

$Y_1$ is O, S or $NR_5$;

M is $NR_3$, O or S;

Ar is a moiety which when included in Formula (I) forms a multi-substituted aromatic or heteroaromatic hydrocarbon or a multi-substituted heterocyclic group;

(m) is zero or positive integer, preferably from about 1 to about 20. More preferably, (m) is zero or one.

$R_{1-3}$ and $R_5$ are independently selected from the group which includes hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and $R_4$ is a polymeric residue.

In some preferred aspects of the invention, the aromatic portion of the polymeric transport form is derived from substituted benzoic acids. In other preferred aspects, $R_4$ is poly(ethylene glycol) residue having a molecular weight of at least about 20,000, (m) is zero or one and $Y_1$ is O. $R_{1-3}$ are preferably each H, methyl or ethyl. In more preferred aspects, $R_{1-3}$ are each H.

Methods of making and using the compounds and conjugates described herein are also provided.

One advantage of the polymeric transport systems of the present invention is the fact that they include substituted aromatic moieties. The artisan thus has the ability to include substituents on the ring to effect the rate of hydrolysis of the prodrug. This technique is an alternative way to achieve an effect similar to that which is achieved using various spacers like amino acids between the polymer residue and attached bioeffective agent to modulate the rate of hydrolysis.

DETAILED DESCRIPTION OF THE INVENTION

Figure 1:
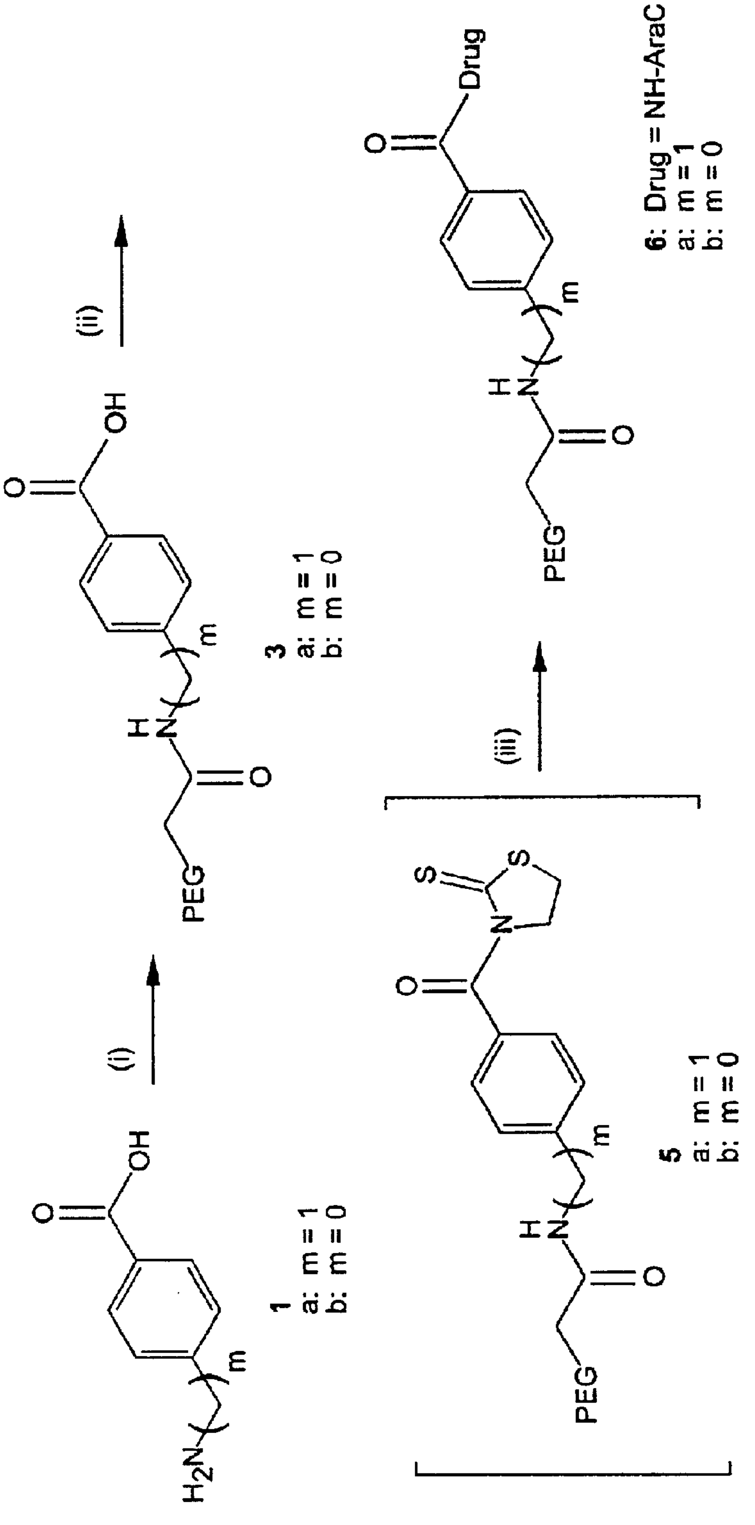
FIGS. 1–2 schematically illustrate methods of synthesis described in the Examples section of the specification.
Figure 2:
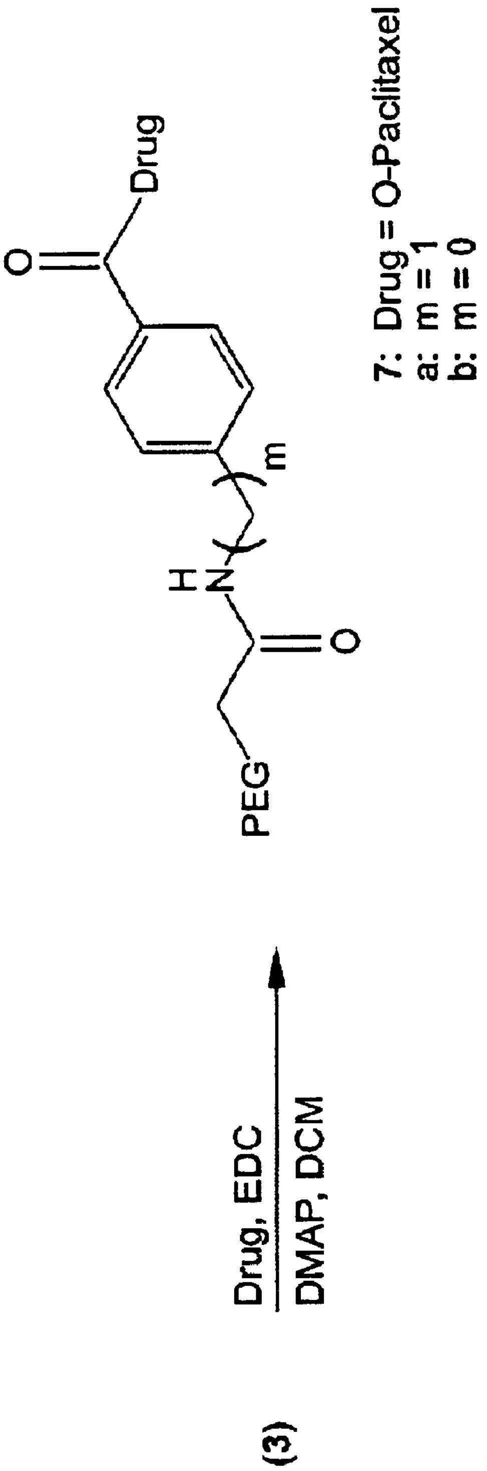

In order that the reader better appreciate the description of the invention, the following definitions are provided:

For purposes of the present invention, the term "residue" shall be understood to mean that portion of a biologically active compound which remains after the biologically active compound has undergone a substitution reaction in which the prodrug carrier portion has been attached.

For purposes of the present invention, the term "alkyl" shall be understood to include straight, branched, substituted, e.g. halo-, alkoxy-, and nitro-$C_{1-12}$ alkyls, $C_{3-8}$ cycloalkyls or substituted cycloalkyls, etc. Lower alkyl shall be understood to be $C_{1-12}$.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromophenyl; aralkyls include moieties such as toluyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo- shall be understood to include fluoro, chloro, iodo and bromo.

The term "sufficient amounts" for purposes of the present invention shall mean an amount which achieves a therapeutic effect as such effect is understood by those of ordinary skill in the art.

As pointed out in the Summary, the invention includes polymeric prodrug transport forms which are of Formulae (I) and (II) as shown below:

(I)

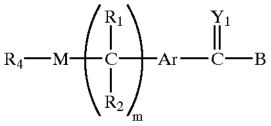

(II)

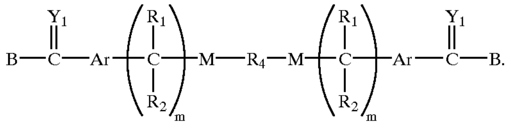

As will be appreciated by the artisan of ordinary skill, the polymer residue portion of (I), $R_4$ preferably includes a capping group located distal to the portion which serves as the point of attachment for the B moiety, e.g. the drug residue or leaving group. The capping group, designated herein as A, can be selected from among hydrogen, $CO_2H$, $C_{1-6}$ alkyl moieties, and (I')

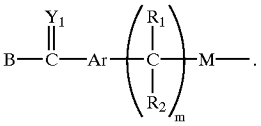

The preferred capping group (I'), of course, allows the composition of Formula (II) to be formed.

One particularly preferred transport form is of the formula:

(II')

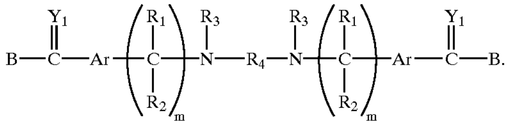

Description of the Ar Moiety

Referring to Formulae (I) and (II), it can be seen that (Ar) is a moiety, which when included in Formula (I), forms a multi-substituted aromatic or heteroaromatic hydrocarbon or a multi-substituted heterocyclic group. A key feature is that the Ar moiety is aromatic in nature. Generally, to be aromatic, the π electrons must be shared within a "cloud" both above and below the plane of a cyclic molecule. Furthermore, the number of π electrons must satisfy the Hückle rule (4n+2). Those of ordinary skill will realize that a myriad of moieties will satisfy the aromatic requirement of the moiety and thus are suitable for use herein. One particularly preferred moiety is is

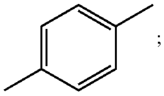

;

other preferred aromatic groups include:

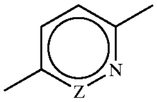 , 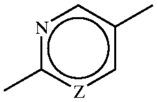 , 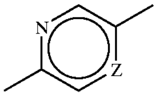 ,

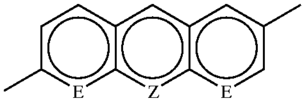 , 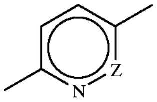 ,

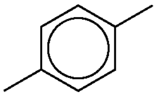 , 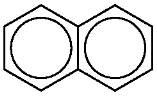 , 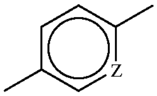 ,

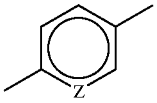 , 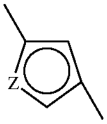 , 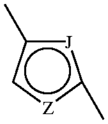 , and

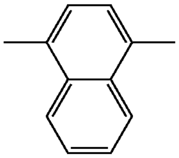

wherein J is O, S, or N—$R_6$; and E and Z are independently C—$R_7$ or N—$R_8$; and $R_{6-8}$ are independently selected from the same group as that which defines $R_1$, but are preferably H or a lower alkyl.

Isomers of the five and six-membered rings are also contemplated as well as benzo- and dibenzo-systems such as anthracine, naphthalene and their related congeners are also contemplated.

Furthermore, the aromatic or heterocyclic structures may optionally be substituted with halogen(s) and/or side chains as those terms are commonly understood in the art. All structures suitable for Ar moieties of the present invention are capable of allowing the substituents on the aromatic group to be aligned within the same plane. Ortho and meta substituted aromatics can also be used.

Substantially Non-Antigenic Polymers

As stated above, $R_4$ is a polymeric residue which is preferably substantially non-antigenic. In preferred aspects of the invention, $R_4$ further includes the previously mentioned capping group A which allows the bis system to be formed. Suitable examples of such polymers include polyalkylene oxides such as polyethylene glycols. The general formula for PEG and its derivatives, i.e.

$$A_2'—O—(CH_2CH_2O)_x—(CH_2)_n—A_2$$

where (x) represents the degree of polymerization (i.e. from about 10 to about 2,300) or number of repeating units in the polymer chain and is dependent on the molecular weight of the polymer, (n) is zero or a positive integer, ($A_2$) is a capping group as defined herein, i.e. an amino, carboxy, carboxyalkyl, halo, $C_{1-6}$ alkyl or other activating group and ($A_2$') is the same as ($A_2$) or another ($A_2$) moiety. Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998". The disclosure of each of the foregoing is incorporated herein by reference. It will be understood that the water-soluble polymer can be functionalized for attachment to the linkage via M, herein. As an example, the PEG portion of the inventive compositions can be one of the following non-limiting compounds:

As an example, the PEG residue portion of the inventive compositions can be selected from the following non-limiting list:

$$—C(=Y_2)—(CH_2)_n—O—(CH_2CH_2O)_x—A,$$

$$—C(=Y_2)—Y_3—(CH_2)_n—O—(CH_2CH_2O)_x—A,$$

$$—C(=Y_2)—NR_{10}—(CH_2)_n—O—(CH_2CH_2O)_x—A,$$

$$—(CR_{11}R_{12})_e—O—(CH_2)_n—O—(CH_2CH_2O)_x—A,$$

and $$—NR_{10}—(CH_2)_n—O—(CH_2CH_2O)_x—A,$$

wherein $Y_2$ and $Y_3$ are independently O, S or $NR_{10}$;

x is the degree of polymerization;

$R_{10}$, $R_{11}$ and $R_{12}$ are independently selected from among H, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

e and n are independently zero, one or two; and

A is a capping group.

In many aspects of the present invention, bis-activated polyethylene glycols are preferred when di-substituted polymer conjugates are desired. The PEG derivatives would thus correspond to the formulae:

$$—C(=Y_2)—(CH_2)_n—O—(CH_2CH_2O)_x—(CH_2)_n—C(=Y_2)—,$$

$$—C(=Y_2)—Y_3—(CH_2)_n—O—(CH_2CH_2O)_x—(CH_2)_n—Y_3—C(=Y_2)—,$$

$$—C(=Y_2)—NR_{10}—(CH_2)_n—O—(CH_2CH_2O)_x—(CH_2)_n—NR_{10}—C(=Y_2)—,$$

$$—(CR_{11}R_{12})_e—O—(CH_2)_n—O—(CH_2CH_2O)_x—(CH_2)_n—O—(CR_{11}R_{12})_e—,$$

and $$—NR_{10}—(CH_2)_n—O—(CH_2CH_2O)_x—(CH_2)_n—NR_{10}—$$

wherein all variables are as set forth above.

Alternatively, polyethylene glycols (PEGs), mono-activated, $C_{1-4}$ alkyl-terminated PAO's such as mono-methyl-terminated polyethylene glycols (mPEG's) are preferred when mono-substituted polymers are desired.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting mPEG-OH to an ethyl ester followed by saponification. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in number average molecular weight, polymers ranging from about 2,000 to about 100,000 are usually selected for the purposes of the present invention. Molecular weights of from about 5,000 to about 45,000 are preferred and 20,000 to about 42,000 are particularly preferred. The number average molecular weight of the polymer selected for inclusion in the prodrug must be sufficient so as to provide sufficient circulation of the prodrug before hydrolysis of the linker. Within the ranges provided above, polymers having molecular weight ranges of at least 20,000 are preferred for many embodiments such as those in which small molecule chemotherapeutic and organic moieties are being delivered.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" and "substantially non-antigenic" shall be understood to include all polymeric materials understood in the art as being substantially non-toxic and not eliciting an appreciable immune response in mammals.

It will be clear from the foregoing that other polyalkylene oxide derivatives of the foregoing, such as the polypropylene glycol acids, etc., as well as other bi-functional linking groups are also contemplated.

Prodrug Candidates

1. Residues of Hydroxyl-containing Compounds a. Camptothecin and Related Topoisomerase I Inhibitors Camptothecin is a water-insoluble cytotoxic alkaloid produced by *Camptotheca accuminata* trees indigenous to China and *nothapodytes foetida* trees indigenous to India. Camptothecin and related compounds and analogs are also known to be potential anticancer or antitumor agents and have been shown to exhibit these activities in vitro and in vivo. Camptothecin and related compounds are also candidates for conversion to the prodrugs of the present invention. Camptothecin and certain related analogues share the structure:

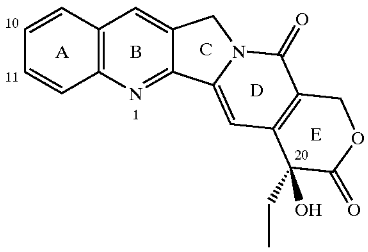

From this core structure, several known analogs have been prepared. For example, the A ring in either or both of the 10- and 11-positions can be substituted with an OH. The A ring can also be substituted in the 9-position with a straight or branched $C_{1-30}$ alkyl or $C_{1-17}$ alkoxy, optionally linked to the ring by a heteroatom i.e. —O or S. The B ring can be substituted in the 7-position with a straight or branched $C_{1-30}$ alkyl or substituted alkyl-, $C_{5-8}$ cycloakyl, $C_{1-30}$ alkoxy, phenyl alkyl, etc., alkyl carbamate, alkyl carbazides, phenyl hydrazine derivatives, amino-, aminoalkyl-, aralkyl, etc. Other substitutions are possible in the C, D and E rings. See, for example, U.S. Pat. Nos. 5,004,758; 4,943,579; Re 32,518, the contents of which are incorporated herein by reference. Such derivatives can be made using known synthetic techniques without undue experimentation. Preferred camptothecin derivatives for use herein include those which include a 20-OH or another OH moiety which is capable of reacting directly with activated forms of the polymer transport systems described herein or to the linking moiety intermediates, e.g. iminodiacetic acid, etc., which are then attached to a polymer such as PEG. Reference to camptothecin analogs herein has been made for purposes of illustration and not limitation.

b. Taxanes and Paclitaxel Derivatives

One class of compounds included in the prodrug compositions of the present invention is taxanes. For purposes of the present invention, the term "taxane" includes all compounds within the taxane family of terpenes. Thus, taxol (paclitaxel), 3'-substituted tert-butoxy-carbonyl-amine derivatives (taxoteres) and the like as well as other analogs which are readily synthesized using standard organic techniques or are available from commercial sources such as Sigma Chemical of St. Louis, Mo. are within the scope of the present invention. These derivatives have been found to be effective anti-cancer agents. Numerous studies indicate that the agents have activity against several malignancies. To date, their use has been severely limited by, among other things, their short supply, poor water solubility and a tendency to cause hypersensitivity. It is to be understood that other taxanes including the 7-aryl-carbamates and 7-carbazates disclosed in commonly assigned U.S. Pat. Nos. 5,622,986 and 5,547,981 can also be included in the prodrugs of the present invention. The contents of the foregoing U.S. patents are incorporated herein by reference. Paclitaxel is a preferred taxane.

c. Additional Biologically-Active Moieties

In addition to the foregoing molecules, the prodrug formulations of the present invention can be prepared using many other compounds. For example, biologically-active compounds such as bis-PEG conjugates derived from compounds such as gemcitabine:

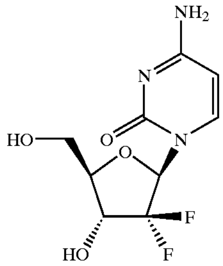

or podophyllotoxin:

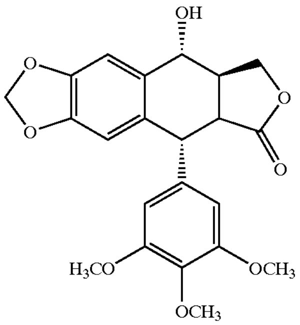

or triazole-based antifungal agents such as fluconazole:

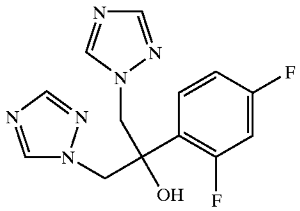

or ciclopirox:

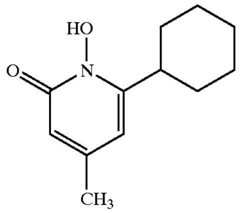

or Ara-C:

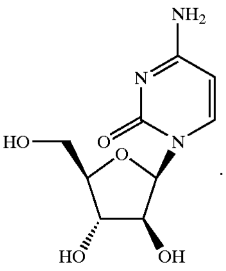

.

The parent compounds selected for prodrug forms need not be substantially water-insoluble, although the polymer-based prodrugs of the present invention are especially well suited for delivering such water-insoluble compounds. Other useful parent compounds include, for example, certain low molecular weight biologically active proteins, enzymes and peptides, including peptido glycans, as well as other antitumor agents; cardiovascular agents such as forskolin; anti-neoplastics such as combretastatin, vinblastine, doxorubicin, maytansine, etc.; anti-infectives such as vancomycin, erythromycin, etc.; anti-fungals such as nystatin, amphotericin B, triazoles, papulocandins, pneumocandins, echinocandins, polyoxins, nikkomycins, pradimicins, benanomicins, etc. see, "Antibiotics That Inhibit Fungal Cell Wall Development" *Annu. Rev. Microbiol.* 1994, 48:471–97, the contents of which are incorporated herein by reference; anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

The foregoing is illustrative of the biologically active moieties which are suitable for the prodrugs of the present invention. It is to be understood that those biologically active materials not specifically mentioned but having suitable ester-forming groups, i.e. hydroxyl moieties, are also intended and are within the scope of the present invention. It is also to be understood that the prodrug conjugates of the present invention may also include minor amounts of compounds containing not only one equivalent of drug and polymer but also a moiety which does not effect bioactivity in vivo. For example, it has been found that in some instances, in spite of reacting diacids with drug molecules having a single linkage point, the reaction conditions do not provide quantitative amounts of prodrugs with two equivalents of drug per polymer. By-products of the reactants can sometimes be formed such as acyl ureas if carbodiimides are used.

2. Residues of Amine-containing Compounds

In some aspects of the invention, B is a residue of an amine-containing compound, a non-limiting list of such suitable compounds include residues of organic compounds, enzymes, proteins, polypeptides, etc. Organic compounds include, without limitation, moieties such as anthracycline compounds including daunorubicin, doxorubicin; p-aminoaniline mustard, melphalan, Ara-C (cytosine arabinoside) and related anti-metabolite compounds, e.g., gemcitabine, etc. Alternatively, B can be a residue of an amine-containing cardiovascular agent, anti-neoplastic, anti-infective, anti-fungal such as nystatin and amphotericin B, anti-anxiety agent, gastrointestinal agent, central nervous system-activating agent, analgesic, fertility agent, contraceptive agent, anti-inflammatory agent, steroidal agent, anti-urecemic agent, vasodilating agent, vasoconstricting agent, etc.

In a preferred aspect of the invention, the amino-containing compound is a biologically active compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds can be similarly modified without undue experimentation. It is to be understood that those biologically active materials not specifically mentioned but having suitable amino-groups are also intended and are within the scope of the present invention.

The only limitations on the types of amino-containing molecules suitable for inclusion herein is that there is available at least one (primary or secondary) amine-containing position which can react and link with a carrier portion and that there is not substantial loss of bioactivity after the prodrug system releases and regenerates the parent compound.

It is noted that parent compounds suitable for incorporation into the prodrug compositions of the invention, may themselves be substances/compounds which are not active after hydrolytic release from the linked composition, but which will become active after undergoing a further chemical process/reaction. For example, an anticancer drug that is delivered to the bloodstream by the prodrug transport system, may remain inactive until entering a cancer or tumor cell, whereupon it is activated by the cancer or tumor cell chemistry, e.g., by an enzymatic reaction unique to that cell.

3. Leaving Groups

In those aspects where B is a leaving group, suitable leaving groups include, without limitations, moieties such as N-hydroxybenzotriazolyl, halogen, N-hydroxyphthalimidyl, p-nitrophenoxy, imidazolyl, N-hydroxysuccinimidyl; thiazolidinyl thione, or other good leaving groups as will be apparent to those of ordinary skill. The synthesis reactions used and described herein will be understood by those of ordinary skill without undue experimentation.

For example, the selective acylation of the anilinic portion of the p-aminobenzoic acid can be carried out with, for example, thiazolidine thione activated polymers, succinimidyl carbonate activated polymers, carboxylic acid activated polymers, blocked amino acid activated derivatives. An acylated intermediate corresponding to compound (I) can be reacted with a reagent such as 4-nitrophenyl chloroformate, disuccinimidyl carbonate (DSC), carbonyldiimid-azole, thiazolidine thione, etc. to provide the desired activated derivative. Once in place, the "activated" form of the PEG-aromatic spacer or blocked amino acid-aromatic spacer is ready for conjugation with an amine- or hydroxyl-containing compound.

It is noted that parent compounds suitable for incorporation into the prodrug compositions of the invention, may themselves be substances/compounds which are not active after hydrolytic release from the linked composition, but which will become active after undergoing a further chemical process/reaction. For example, an anti-cancer drug that is delivered to the bloodstream by the prodrug transport system, may remain inactive until entering a cancer or tumor cell, whereupon it is activated by the cancer or tumor cell chemistry, e.g., by an enzymatic reaction unique to that cell.

After conjugation, the remaining portion of the amine-containing or hydroxyl-containing compound is referred to as the residue of the unconjugated compound.

Synthesis of the Polymeric Prodrug Transport System

Synthesis of representative polymer prodrugs is set forth in the Examples. Generally, however, in one preferred method of preparing the prodrug transport systems, the mono or bis polymer residue is first attached to the aminoalkyl benzoic or aromatic acid to form the polymer-aromatic acid. The intermediate is then functionalized with a reactive leaving group to facilitate conjugation with the amino or hydroxyl containing biologically active compound or target under conditions sufficient to provide a polymeric conjugate. See formulae III and III' below.

(III)

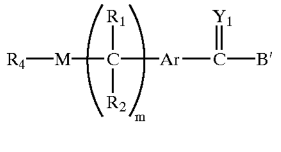

-continued (III')

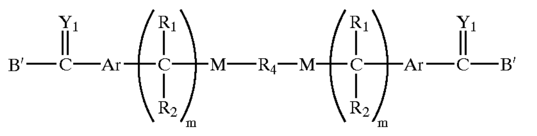

wherein B' is a leaving group and all other variables are as defined above. It will be noted that in (III') $R_4$ is shown with the polymer capping group IV:

(IV)

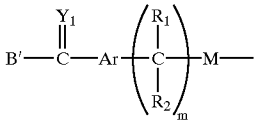

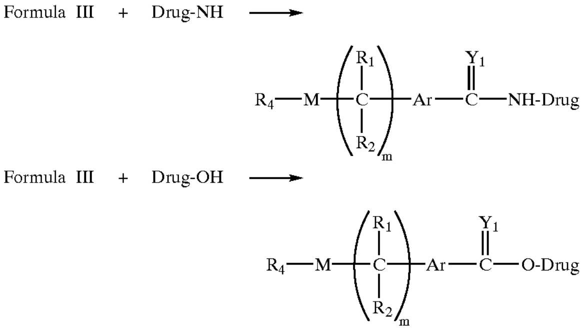

Alternatively, the substituted benzoic acid derivative can first be reacted with the amino or hydroxyl containing bioactive target. Thereafter, this intermediate is reacted with a suitably activated the polymeric residue such as a PEG diacid in the presence of a coupling agent such as DIPC in order to form the final product.

Attachment of the bifunctional spacer containing the aromatic-drug component to the polymer portion is preferably carried out in the presence of a coupling agent. A non-limiting list of suitable coupling agents include 1,3-diisopropylcarbodiimide (DIPC), any suitable dialkyl carbodiimides, 2-halo-1-alkyl-pyridinium halides, (Mukaiyama reagents), 1-(3-dimethylaminopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

Preferably the substituents are reacted in an inert solvent such as methylene chloride, chloroform, DMF or mixtures thereof. The reaction also preferably is conducted in the presence of a base, such as dimethylaminopyridine (DMAP), diisopropylethylamine, pyridine, triethylamine, etc. to neutralize any acids generated and at a temperature from 0° C. up to about 22° C. (room temperature). Regardless of the synthesis selected, some of the preferred compounds which result from the synthesis techniques described herein include:

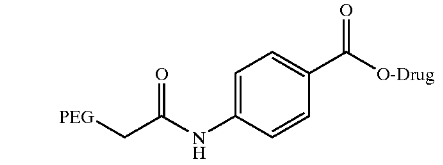

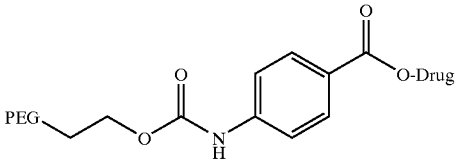

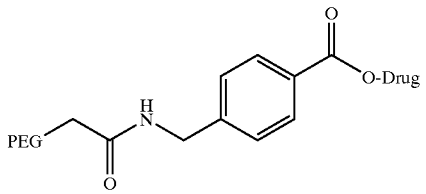

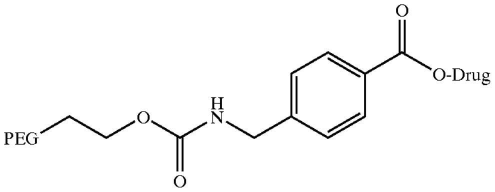

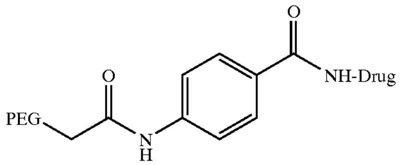

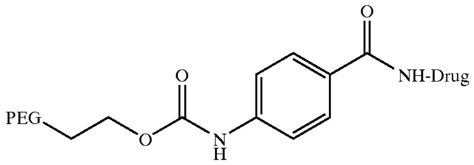

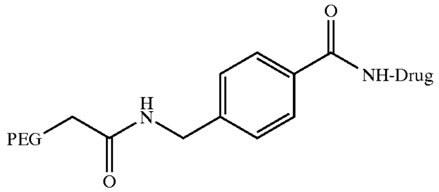

and

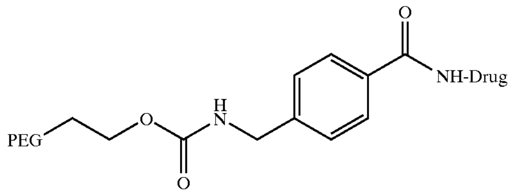

Di-substituted examples of the inventive compounds include:
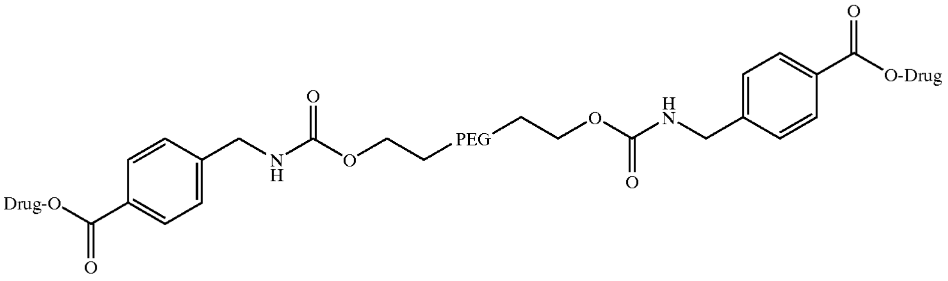
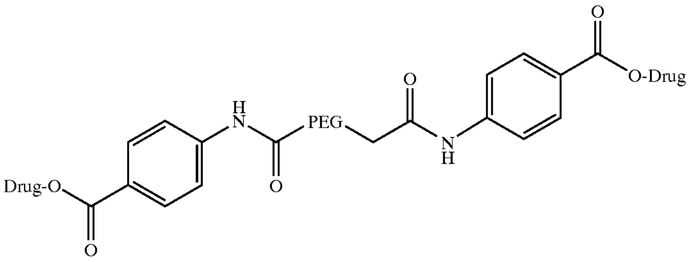
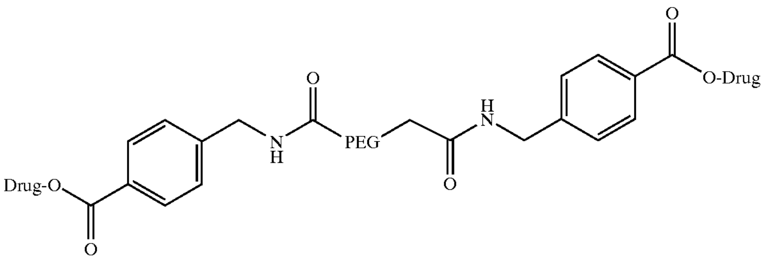
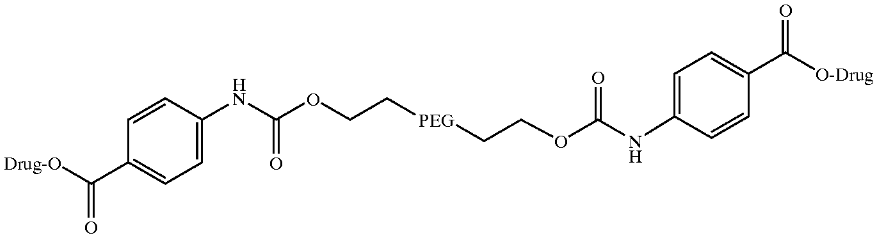
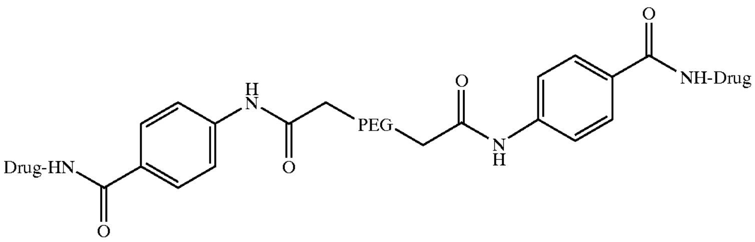
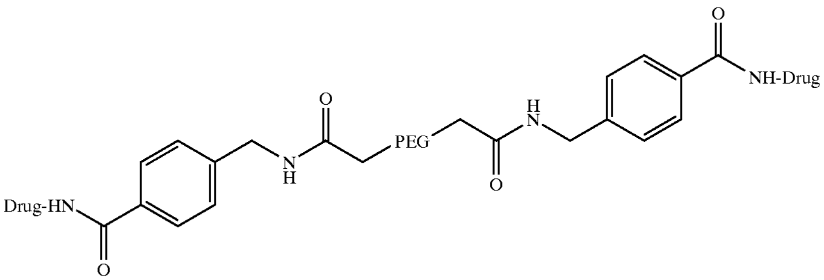

-continued

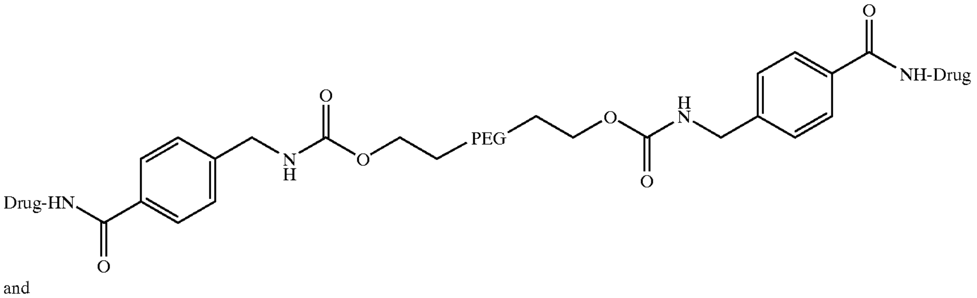

and

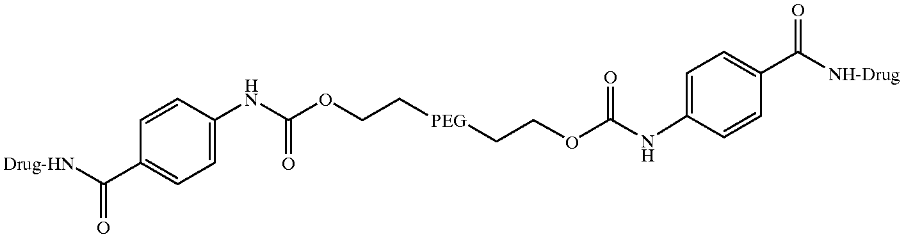

It will be understood from the formulae above that the "Drug-O—" and "Drug-NH—" represent the residue of the hydroxyl and amino-containing moieties.

In Vivo Diagnostics

A further aspect of the invention provides the conjugates of the invention optionally prepared with a diagnostic tag linked to the transport enhancer described above, wherein the tag is selected for diagnostic or imaging purposes. Thus, a suitable tag is prepared by linking any suitable moiety, e.g., an amino acid residue, to any art-standard emitting isotope, radio-opaque label, magnetic resonance label, or other non-radioactive isotopic labels suitable for magnetic resonance imaging, fluorescence-type labels, labels exhibiting visible colors and/or capable of fluorescing under ultraviolet, infrared or electrochemical stimulation, to allow for imaging tumor tissue during surgical procedures, and so forth. Optionally, the diagnostic tag is incorporated into and/or linked to a conjugated therapeutic moiety, allowing for monitoring of the distribution of a therapeutic biologically active material within an animal or human patient.

In a still further aspect of the invention, the inventive tagged conjugates are readily prepared, by art-known methods, with any suitable label, including, e.g., radioisotope labels. Simply by way of example, these include $^{131}$Iodine, $^{125}$Iodine, $^{99m}$Technetium and/or $^{111}$Indium to produce radioimmunoscintigraphic agents for selective uptake into tumor cells, in vivo. For instance, there are a number of art-known methods of linking peptide to Tc-99m, including, simply by way of example, those shown by U.S. Pat. Nos. 5,328,679; 5,888,474; 5,997,844; and 5,997,845, incorporated by reference herein.

Broadly, for anatomical localization of tumor tissue in a patient, the conjugate tag is administered to a patient or animal suspected of having a tumor. After sufficient time to allow the labeled immunoglobulin to localize at the tumor site(s), the signal generated by the label is detected, for instance, visually, by X-ray radiography, computerized transaxial tomography, MRI, by instrumental detection of a luminescent tag, by a photo scanning device such as a gamma camera, or any other method or instrument appropriate for the nature of the selected tag. The detected signal is then converted to an image or anatomical and/or physiological determination of the tumor site. The image makes it possible to locate the tumor in vivo and to devise an appropriate therapeutic strategy. In those embodiments where the tagged moiety is itself a therapeutic agents, the detected signal provides evidence of anatomical localization during treatment, providing a baseline for follow-up diagnostic and therapeutic interventions.

Methods of Treatment

Another aspect of the present invention provides methods of treatment for various medical conditions in mammals. The methods include administering to the mammal in need of such treatment, an effective amount of a composition of the invention, as described herein, such as a prodrug of doxorubicin. The prodrug compositions are useful for, among other things, treating diseases which are similar to those which are treated with the parent compound, e.g. enzyme replacement therapy, neoplastic disease, reducing tumor burden, preventing metastasis of neoplasms and preventing recurrences of tumor/neoplastic growths in mammals. The amount of the prodrug that is administered will depend upon the amount of the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, prodrug polymeric derivatives of nitrogen mustard derivatives are administered in amounts ranging from about 5 to about 500 mg/m$^2$ per day. The range set forth above is illustrative and those skilled in the art will determine the optimal dosing of the prodrug selected based on clinical experience and the treatment indication. Actual dosages will be apparent to the artisan without undue experimentation.

The compositions, including prodrugs, of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like. Such administration may also be by infusion into a body space or cavity, as well as by inhalation and/or intranasal routes. In preferred aspects of the invention, however, the prodrugs are parenterally administered to mammals in need thereof.

EXAMPLES

The following examples serve to provide further appreciation of the invention but are not meant in any way to restrict the effective scope of the invention. The underlined and bold-faced numbers recited in the Examples correspond to those shown in the Figures.

Experimental

General.

All reactions were run under an atmosphere of dry nitrogen or argon. Commercial reagents were used without further purification. All PEG compounds were dried under vacuum or by azeotropic distillation (toluene) prior to use. $^{13}C$ NMR spectra were obtained at 67.80 MHz on the JNM GSX-270 or 75.46 MHz on the Varian Mercury VX-300 instrument using deuteriochloroform as solvent unless specified. Chemical shifts (δ) are reported in parts per million (ppm) downfield from tetramethylsilane (TMS). All PEG conjugated compounds were dissolved (~15 mg/mL) in sterile saline (0.9%) for injection prior to in vivo drug treatments and were given as their ara-C equivalents (absolute amount of ara-C given).

Abbreviations.

DCM (dichloromethane), DIEA (N,N-diisopropylethylamine), DMAP (4-(dimethylamino) pyridine), EDC (1-ethyl-3-(3-dimethylaminopropyl)-carbodiimide), HOBT (1-hydroxybenzotriazole), IPA (2-propanol).

Example 1

PEG Aromatic Amides (3a and 3b).

A mixture of 2 (5.0 g, 0.125 mmol), 1a or 1b (0.496 mmol) in anhydrous pyridine (50 mL) was stirred at 45° C. overnight under argon atmosphere. The mixture was cooled to room temperature and concentrated in vacuo followed by the recrystallization from IPA (500 mL) to give 3a from 1a and 3b from 1b.

PEG 4-aminomethylbenzoic Acid (3a).

96% yield: $^{13}C$ NMR δ 41.46, 66.91–70.71 (PEG), 126.57, 128.71, 129.22, 142.95, 166.75, 169.35.

PEG 4-aminobenzoic Acid (3b).

83% yield: $^{13}C$ NMR δ 69.91–70.89 (PEG), 118.36, 126.67, 130.22, 140.64, 167.21, 167.94.

Example 2

PEG Aromatic Amide Thiazolidinyl Thione Imide (5a and 5b).

A mixture of 3a or 3b (0.099 mmol), 2-mercaptothiazoline (4, 71 mg, 0.60 mmol), EDC-HCl (78 mg, 0.40 mmol), and DMAP (97 mg, 0.79 mmol) in anhydrous DCM (80 mL) was stirred overnight at room temperature. The mixture was concentrated in vacuo and the residue recrystallized from IPA to give 5a from 3a and 5b and 3b. The NMR confirmed the activation of the benzoic acid and the presence of 2-mercaptothiazoline in almost 1:1 ratio. These intermediates were used as is.

Example 3

PEG Aromatic Spacer ara-C (6a and 6b).

A mixture of activated imide 5a or 5b (0.074 mmol), ara-C (108 mg, 0.44 mmol), and DMAP (72 mg, 0.59 mmol) in anhydrous pyridine (30 mL) was stirred overnight at 45° C. The mixture was concentrated in vacuo and the residue was recrystallized from IPA to give 6a from 5a and 6b from 5b. The amount of Ara-C present in this compound as measured by UV assay was given by weight %.

PEG ara-C 4-aminomethylbenzenamide (6a).

94% yield, 1.18% of ara-C present: $^{13}C$ NMR δ 42.42, 59.59, 61.70, 62.22, 64.11, 67.51, 68.64, 69.30–73.16 (PEG), 74.30, 75.86, 77.57, 77.69, 82.21, 86.58, 88.48, 96.16, 128.02, 128.11, 129.13, 130.35, 1455.85, 147.55, 148.23, 170.73.

PEG ara-C 4-aminobenzenamide (6b).

90% yield, 1.03% of ara-C present: $^{13}C$ NMR δ 65.21, 70.90–70.94 (PEG), 76.30, 78.86, 86.58, 88.48, 96.16, 118.15, 128.07, 128.24, 130.35, 145.85, 147.55, 148.23, 170.80.

Example 4

PEG Paclitaxel 4-aminobenzenamide (7a).

EDC-HCl (38 mg, 0.2 mmol) was added to a solution of 3a (1 g, 0.025 mmol), paclitaxel (85 mg, 0.1 mmol), and DMAP (37 mg, 0.3 mmol) in anhydrous DCM (20 mL) and the mixture stirred at 0° C. to room temperature overnight. The mixture was concentrated in vacuo and the residue recrystallized from IPA to give 0.86 g (86%) of product. The amount of paclitaxel present in this compound measured by UV assay was 4.06% wt/wt: $^{13}C$ NMR δ 3.01, 14.19, 20.18, 21.48, 22.07, 26.17, 29.03, 35.10, 41.66, 42.55, 45.08, 52.54, 57.75, 69.97–71.87 (PEG), 74.56, 75.77, 79.89, 84.66, 126.61, 127.75, 128.03, 128.43, 129.50, 132.59, 133.24, 133.72, 135.65, 141.89, 144.58, 164.67, 166.08, 166.58, 167.62, 169.75, 170.23, 202.13.

Example 5

In vitro and in vivo Data for Compounds 6a and 6b.

In this Example, in vivo and in vitro data are presented and compared to unmodified Ara-C.

In Vivo

Athymic nude mice were implanted subcutaneous with a 4–5 $mm^3$ tissue fragment of LX-1 (solid human lung Tumor) collected from donor mice. The tumor trocar site was observed twice weekly and measured once palpable. The tumor volume for each mouse was determined by measuring two dimensions with calipers and calculated using the formula: tumor volume=(length×width$^2$)/2. When tumors reached the average volume of 90 $mm^3$, the mice were divided into their experimental groups which consisted of unmodified Ara-C and PEG-Ara-C (Compounds 6a and 6b). The mice were sorted to evenly distribute tumor size, grouped into 4 to 6 mice/group, and ear punched for permanent identification. Drugs were administered intravenously q3d×4 (Day 1, 4, 7 and 10) via the tail vein at an approximate rate of 0.5 mL per minute. Compounds were given both at an equal molar basis (absolute amount of active) of 20 mg/kg and at close their respective MTD (Ara-C, 100 mg/kg/dose (toxicity); 6a and 6b, 40 mg/kg/dose (volume). Mouse weight and tumor size were measured at the beginning of study and twice weekly through week 4. Drug effectiveness was determined by comparing tumor growth in treated versus untreated (no vehicle) control mice. Five types of endpoints were used as the basis for comparison: (a) mean tumor volumes at Day 28; (b) mean percent change in individual tumor volumes from initial; (c) percent tumor growth inhibition which was calculated from the quotient of the median tumor volume of the treatment group divided by the median tumor volume of the control group ((T/C-1)×100)when the latter reached 1000 $mm^3$.

Results

| Compound | $t_{1/2}$ (h)[a] Rat Plasma | $IC_{50}$ (nM)[a] P388/O | % Tumor Growth Inhibition[b] |
|---|---|---|---|
| Ara-C | — | 10 | 26.2 (100 mg/kg) |
| Compound 6a | 65 | 122 | — |
| Compound 6b | 75 | 1190 | 12.3 (20 mg/kg) |

[a]All experiments were done at 37° C. in duplicate and $t_{1/2}$ was measured by the disappearance of PEG derivatives. Standard deviation of measurements = ±10%.
[b]Mean baseline tumor volume was 1000 $mm^3$.

In vitro Bioassay

A series of in vitro assays were conducted to determine the $IC_{50}$ for unmodified Ara-C and compound 10 using the P388/O (murine lymphoid neoplasm, Southern Research Institute) cell line. The P388/0 cells were grown in RPMI 1640 medium (Whittaker Bioproducts, Walkersville, Md.)+10% FBS (Hyclone Inc., Logan Utah). Bioassays were performed in their respective media containing antibiotics and fungizone.

Ara-C was dissolved in DMSO and diluted to the appropriate concentration in culture media. The individual PEG-Ara-C compound was dissolved in water and diluted to the appropriate concentrations in culture media.

The assays were performed in duplicate in 96-well microtiter cell culture plates. Two fold serial dilution of the compounds were done in the microtiter plates. Cells were detached by incubating with 0.1% Trypsin/Versene at 37°. Trypsin was inactivated by adding the appropriate media for each cell line containing 10% FBS. To each well of the microtiter plates, 10,000 cells were added. After three days, cell growth was measured by addition of a metabolic indicator dye, Alamar Blue, according to the manufacturer's protocol. The $IC_{50}$ value for the test compound and reference compound are provided above in the Table.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

We claim:

1. A compound comprising the structure:

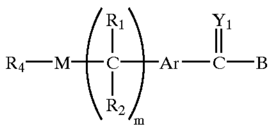

wherein

B is selected from the group consisting of OH, leaving groups, residues of amine-containing moieties and a residues of hydroxyl-containing moieties;

$Y_1$ is selected from the group consisting of O, S, and $NR_5$;

M is selected from the group consisting of $NR_3$, O and S;

Ar is a multi-substituted aromatic or heteroaromatic hydrocarbon or a multi-substituted heterocyclic group;

(m) is zero or a positive integer;

$R_{1-3}$ and $R_5$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroakoxy; and $R_4$ is a polymeric residue having a number average molecular weight of from about 2,000 to about 100,000 Daltons.

2. The compound of claim 1, wherein $R_4$ further includes a capping group A, selected from the group consisting of hydrogen, $CO_2H$, $C_{1-6}$ alkyl moieties, and

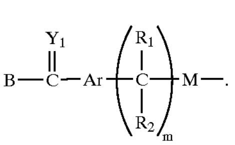

3. A compound of claim 2, of the formula:

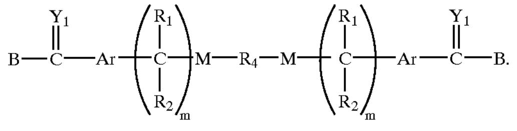

4. A compound of claim 3, of the formula:

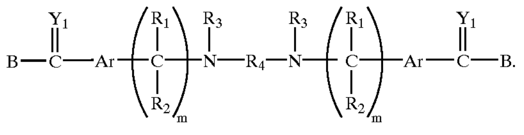

5. The compound of claim 1, wherein $R_1$ $R_2$ and $R_3$ are independently selected from the group consisting of H, methyl and ethyl.

6. The compound of claim 5, wherein $R_1$ $R_2$ and $R_3$ are each H.

7. The compound of claim 1, wherein $Y_1$ is O.

8. The compound of claim 1, wherein the aromatic moiety is selected from the group consisting of:

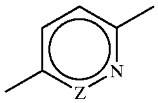 , 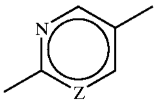 , 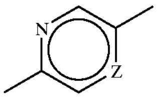 ,

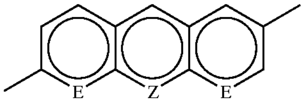 , 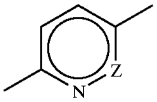 ,

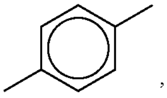 , 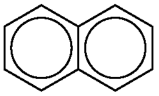 , 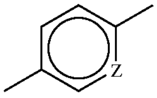 ,

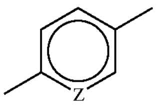 , 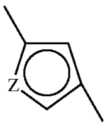 , 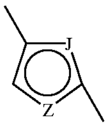 , and

-continued

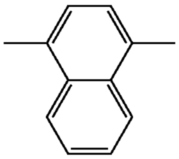

wherein J is O, S, or N—$R_6$; and E and Z are independently C—$R_7$ or N—$R_8$; and $R_{6\text{-}8}$ are independently selected from the same group as that which defines $R_1$.

9. The compound of claim 1, wherein Ar is

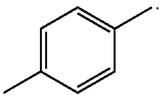

10. The compound of claim 1, wherein B is a residue of an amine-containing moiety.

11. The compound of claim 1, wherein B is a residue of an hydroxyl-containing moiety.

12. The compound of claim 1, wherein B is a leaving group selected from the group consisting of N-hydroxybenzotriazolyl, halogen, N-hydroxyphthalimidyl, p-nitrophenoxy, imidazolyl, N-hydroxysuccinimidyl, thiazolidinyl thione, and an acid activating group.

13. The compound of claim 1 wherein B is a residue of a member of the group consisting of paclitaxel, paclitaxel derivatives, anthracyclines, daunorubicin, doxorubicin, p-hydroxyaniline mustard, Ara-C, cytosine arabinoside and gemcitabine.

14. The compound of claim 1, wherein B is a residue of an enzyme, protein or peptide.

15. The compound of claim 1, wherein $R_4$ has a number average molecular weight of from about 5,000 to about 45,000 Daltons.

16. The compound of claim 15, wherein $R_4$ has a number average molecular weight of from about 20,000 to about 42,000 Daltons.

17. The compound of claim 1, wherein $R_4$ is selected from the group consisting of:

$—C(=Y_2)—(CH_2)_n—O—(CH_2CH_2O)_x—A$, $—C(=Y_2)—Y_3—(CH_2)_n—O—(CH_2CH_2O)_x—A$, $—C(=Y_2)—NR_{10}—(CH_2)_n—O—(CH_2CH_2O)_x—A$, $—(CR_{11}R_{12})_e—O—(CH_2)_n—O—(CH_2CH_2O)_x—A$, and $—NR_{10}—(CH_2)_n—O—(CH_2CH_2O)_x—A$, wherein $Y_2$ and $Y_3$ are independently O, S or $NR_{10}$;

x is the degree of polymerization ranging from about 10 to about 2,300;

$R_{10}$, $R_{11}$ and $R_{12}$ are independently selected from among H, $C_{1\text{-}6}$ alkyls, $C_{3\text{-}12}$ branched alkyls, $C_{3\text{-}8}$ cycloalkyls, $C_{1\text{-}6}$ substituted alkyls, $C_{3\text{-}8}$ substituted cycloalkyls, aryls, substituted aryls, aralkyls, $C_{1\text{-}6}$ heteroalkyls, substituted $C_{1\text{-}6}$ heteroalkyls, $C_{1\text{-}6}$ alkoxy, phenoxy and $C_{1\text{-}6}$ heteroalkoxy;

e and n are independently zero, one or two; and

A is a capping group.

18. The compound of claim 1, wherein $R_4$ is selected from the group consisting of:

$—C(=Y_2)—(CH_2)_n—O—(CH_2CH_2O)_x—(CH_2)_n—C(=Y_2)—$, $—C(=Y_2)—Y_3—(CH_2)_n—O—(CH_2CH_2O)_x—(CH_2)_n—Y_3—C(=Y_2)—$, $—C(=Y_2)—NR_{10}—(CH_2)_n—O—(CH_2CH_2O)_x—(CH_2)_n—NR_{10}—C(=Y_2)—$, $—(CR_{11}R_{12})_e—O—(CH_2)_n—O—(CH_2CH_2O)_x—(CH_2)_n—O—(CR_{11}R_{12})_e—$, and $—NR_{10}—(CH_2)_n—O—(CH_2CH_2O)_x—(CH_2)_x—NR_{10}—$ wherein $Y_2$ and $Y_3$ are independently O, S or $NR_{10}$;

x is the degree of polymerization ranging from about 10 to about 2,300;

$R_{10}$, $R_{11}$ and $R_{12}$ are independently selected from among H, $C_{1\text{-}6}$ alkyls, $C_{3\text{-}12}$ branched alkyls, $C_{3\text{-}8}$ cycloalkyls, $C_{1\text{-}6}$ substituted alkyls, $C_{3\text{-}8}$ substituted cycloalkyls, aryls, substituted aryls, aralkyls, $C_{1\text{-}6}$ heteroalkyls, substituted $C_{1\text{-}6}$ heteroalkyls, $C_{1\text{-}6}$ alkoxy, phenoxy and $C_{1\text{-}6}$ heteroalkoxy;

e and n are independently zero, one or two; and

A is a capping group.

19. The compound of claim 1, wherein $R_4$ comprises a polyalkylene oxide.

20. The compound of claim 19, wherein said polyalkylene oxide comprises polyethylene glycol.

21. A compound of claim 1 selected from the group consisting of:

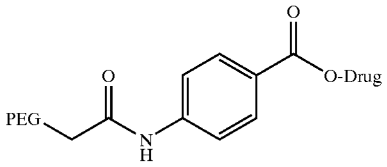

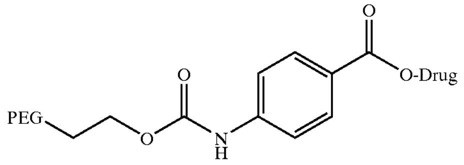

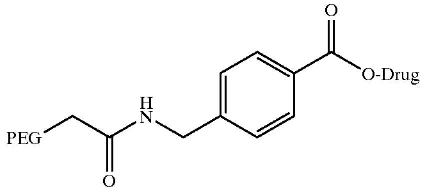

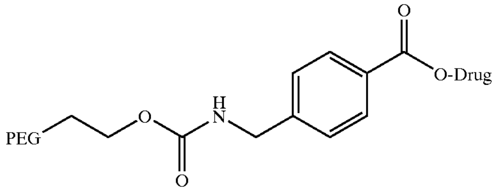

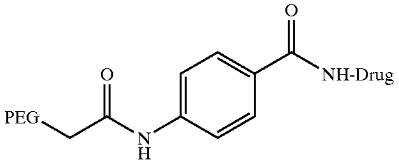

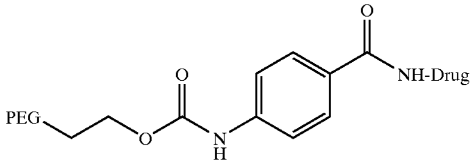

-continued
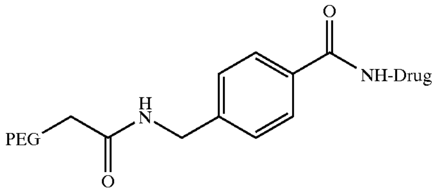
and
-continued
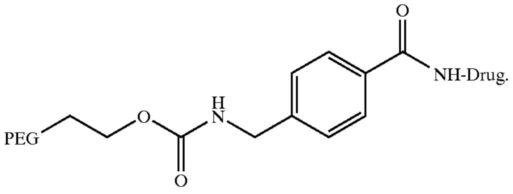
wherein the PEG has a molecular weight of at least 20,000.
22. A compound of claim 1 selected from the group consisting of:
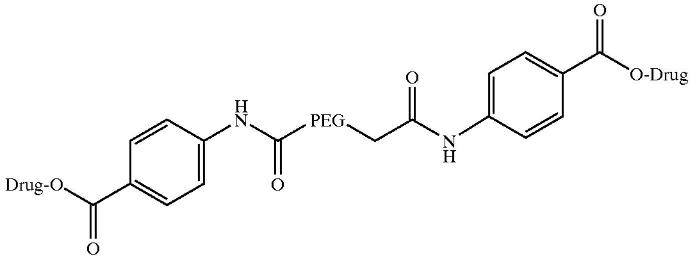
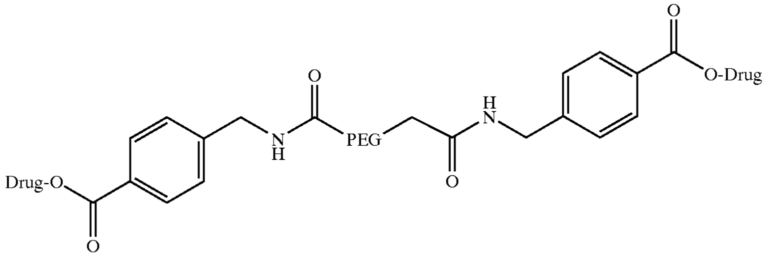
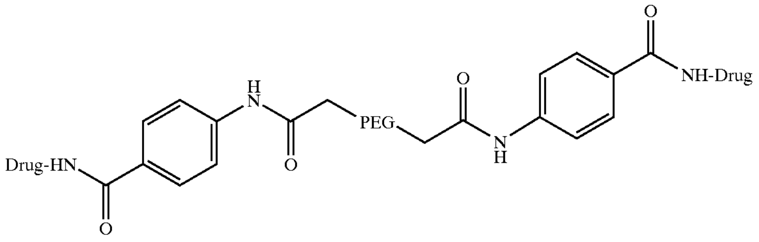
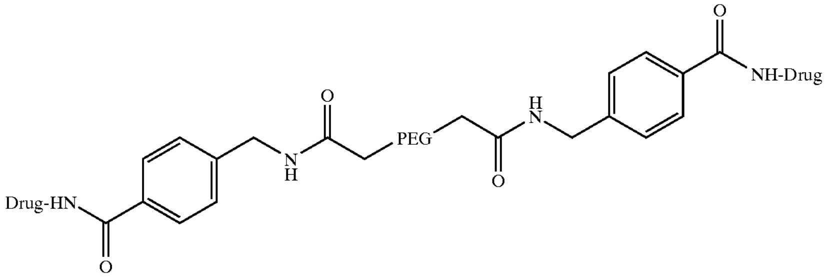
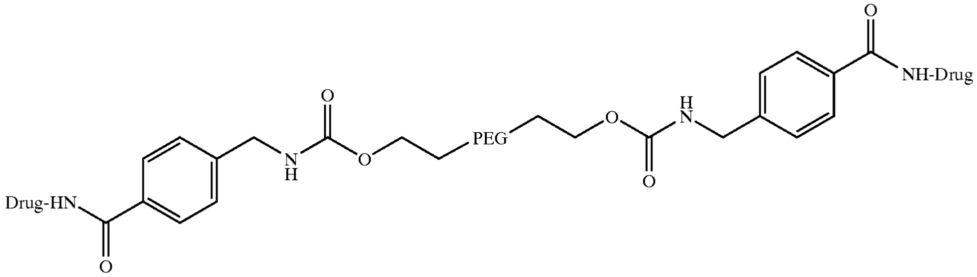

-continued
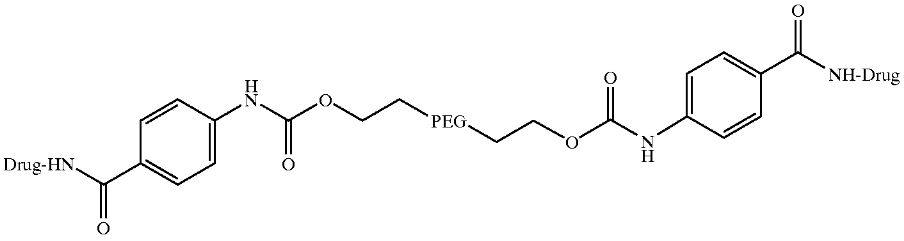
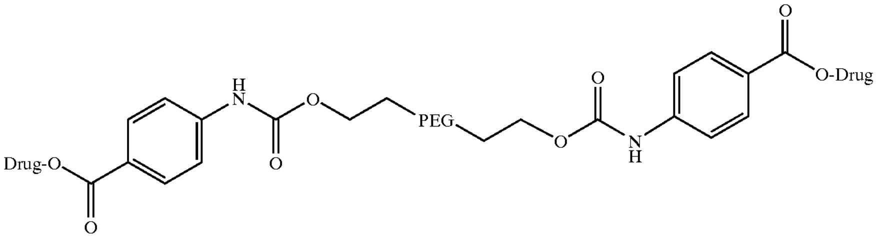
and
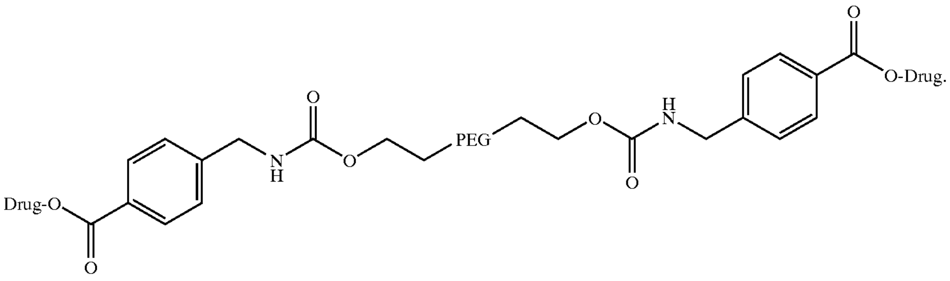
23. The compound of claim 1, wherein m is zero.
24. The compound of claim 1, wherein m is one.
* * * * *